United States Patent
Grupp et al.

(10) Patent No.: US 10,751,443 B2
(45) Date of Patent: Aug. 25, 2020

(54) BONE REPLACEMENT MATERIALS, METHOD FOR PRODUCING A BONE REPLACEMENT MATERIAL AND MEDICAL KITS FOR THE TREATMENT OF BONE DEFECTS

(71) Applicant: Aesculap AG, Tuttlingen (DE)

(72) Inventors: Thomas Grupp, Denkingen (DE); Thomas Hagen, Tuttlingen (DE); Wolfgang Abele, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 15/574,300

(22) PCT Filed: May 6, 2016

(86) PCT No.: PCT/EP2016/060218
§ 371 (c)(1),
(2) Date: Mar. 26, 2018

(87) PCT Pub. No.: WO2016/184699
PCT Pub. Date: Nov. 24, 2016

(65) Prior Publication Data
US 2018/0221533 A1 Aug. 9, 2018

(30) Foreign Application Priority Data
May 15, 2015 (DE) .......................... 10 2015 209 007

(51) Int. Cl.
| | | |
|---|---|---|
| *A61F 2/28* | (2006.01) | |
| *A61L 27/12* | (2006.01) | |
| *A61L 24/00* | (2006.01) | |
| *A61L 27/42* | (2006.01) | |
| *A61L 27/56* | (2006.01) | |
| *A61F 2/30* | (2006.01) | |

(52) U.S. Cl.
CPC ............ *A61L 24/0063* (2013.01); *A61F 2/28* (2013.01); *A61L 24/0052* (2013.01); *A61L 27/42* (2013.01); *A61L 27/56* (2013.01); *A61F 2002/2835* (2013.01); *A61F 2002/30303* (2013.01); *A61F 2310/00293* (2013.01); *A61L 24/001* (2013.01); *A61L 24/0073* (2013.01); *A61L 27/12* (2013.01); *A61L 2430/02* (2013.01)

(58) Field of Classification Search
CPC .... A61F 2002/2835; A61F 2002/30303; A61F 2310/00293; A61F 2/28; A61L 2430/02; A61L 24/001; A61L 24/0052; A61L 24/0063; A61L 24/0073; A61L 27/12; A61L 27/42; A61L 27/56
See application file for complete search history.

(56) References Cited

U.S. PATENT DOCUMENTS

| | | |
|---|---|---|
| 4,309,488 A | 1/1982 | Heide et al. |
| 4,629,464 A | 12/1986 | Takata et al. |
| 4,654,314 A | 3/1987 | Takagi et al. |
| 6,340,648 B1 | 1/2002 | Imura et al. |
| 6,642,285 B1 | 11/2003 | Bohner |
| 6,905,516 B1 | 6/2005 | Lemaitre et al. |
| 7,393,405 B2 | 7/2008 | Bohner |
| 8,741,053 B2 | 6/2014 | Shoji |
| 9,764,057 B2 | 9/2017 | Nies |
| 2003/0050171 A1 | 3/2003 | Myoi et al. |
| 2003/0167093 A1* | 9/2003 | Xu .................. A61L 27/425 623/23.56 |
| 2010/0185299 A1 | 7/2010 | Nies |

FOREIGN PATENT DOCUMENTS

| | | |
|---|---|---|
| CN | 102085123 | 6/2011 |
| DE | 60000877 | 8/2003 |
| DE | 102012213246 | 1/2014 |
| JP | 2004-097259 | 4/2004 |
| JP | 2004-329458 | 11/2004 |
| WO | 20130153185 | 10/2013 |

OTHER PUBLICATIONS

English translation by Google Patents of DE 102013206491; Oct. 31, 2013 11 pages (Year: 2013).*

* cited by examiner

*Primary Examiner* — Ernest V Arnold
(74) *Attorney, Agent, or Firm* — Lewis Kohn & Walker LLP; David M. Kohn

(57) ABSTRACT

A bone replacement material having reinforcing elements and a modelable mass which is curable on contact with water or an aqueous liquid. as well as a process for producing a bone replacement material, to a further bone replacement material and to medical kits for treatment of bone defects.

23 Claims, No Drawings

BONE REPLACEMENT MATERIALS, METHOD FOR PRODUCING A BONE REPLACEMENT MATERIAL AND MEDICAL KITS FOR THE TREATMENT OF BONE DEFECTS

The invention relates to bone replacement materials, to a production process for a bone replacement material and to medical kits for treatment of bone defects.

The treatment of bone defects is typically based on the use of implants and bone replacement materials.

In the treatment of osseous joint defects—depending on the severity of the defect—as well as the actual joint implant, an implant is additionally used to fill the defect, i.e. to bridge the bone defect. The latter is positioned here between the joint implant and the still-healthy bone. Alternatively, it is also possible to insert a bone replacement material between the joint implant and the intact bone.

Implants for bridging bone defects have a geometrically exactly defined shape and require corresponding preparation of the bone defect for it to be incorporated into the bone. This is associated with a high level of complexity and—depending on the type of defect—is not always achievable.

An additional factor is that the mechanical properties of the implants intended for bridging of bone defects are frequently not comparable to those of an osseous structure. This is especially true of metallic implants. The transitions from metal to bone are subject to significant fluctuations in load, which complicates or even prevents long-term fusion with bone tissue and hence any reinforcing function of the implant.

Ceramic implants for treatment of bone defects are known, for example, from publications DE 28 27 529 C2, U.S. Pat. No. 4,654,314, DE 35 31 144 C2, DE 600 00 877 T2, DE 600 33 025 T2, DE 100 18 394 B4 and DE 602 15 895 T2. These implants generally consist of calcium phosphate compounds. Calcium phosphate is an important constituent of bone tissue. The mechanical properties of ceramic implants are therefore more comparable to those of natural bone tissue than to the mechanical properties of metallic implants.

However, ceramic implants—just like metallic implants—are afflicted by the drawback that they generally cannot be fitted to a defect shape. The situation is also comparable with regard to implants that have already been inserted. There is therefore no way of working or adapting the implants within the scope of revision surgery. Instead, it is necessary in many cases to completely remove the implants, increasing the size of the bone defects.

DE 10 2012 213 246 A1 discloses reinforcing elements in the form of oligopods for treatment of bone defects. Even though the reinforcing elements described constitute a high-performance alternative for treatment of bone defects, complete filling of the bone defects—depending on the defect shape—can prove to be difficult.

As an alternative to the implants described to date, what are called bone replacement materials are used for treatment, especially bridging, of bone defects. The bone replacement materials may be natural or synthetic (artificial) bone replacement materials.

Examples of natural bone replacement materials are bone flakes and bone chips. It is disadvantageous that these bone replacement materials can no longer be fixed adequately within a defect over and above a certain amount. There is the risk that individual bone flake particles or chips will become detached from a composite structure formed with other bone flake particles or chips, which reduces the load-bearing capacity of the bone replacement material in the defect region.

The synthetic or artificial bone replacement materials frequently comprise bone cement components which set in a cement-like manner on contact with water. Corresponding bone replacement materials are known, for example, from EP 2 170 245 B1, DE 11 2010 001 628 T5 and DE 603 05 036 T2.

Like bone flakes or chips, however, synthetic bone replacement materials are also afflicted by the drawback that they have limitations with regard to their load-bearing capacity. This is especially true in the case of absorbable bone replacement materials. Especially in the case of treatment of joint defects, there is therefore a risk that forces that act on a joint implant installed in the body will be introduced into the remaining healthy bone only inadequately via the bone replacement materials. The bone replacement materials cannot absorb the forces and fail. This can lead to failure of the implant bearing and hence to loosening of the implant.

It was therefore an object of the present invention to provide bone replacement materials that avoid the drawbacks mentioned at the outset as far as possible. It was a further object of the invention to provide a process for producing a bone replacement material and medical kits.

These objects are achieved by a bone replacement material having the features of independent claim 1, by a process for producing a bone replacement material according to independent claim 24, and by a medical kit according to independent claim 25. Preferred embodiments are defined in the dependent claims. The wording of all claims is hereby incorporated into the present description by explicit reference. Further subjects of the invention are disclosed in the description.

In a first aspect, the invention relates to a bone replacement material or a bone substitute.

The bone replacement material is preferably envisaged for use in the treatment, especially bridging, of bone defects. In other words, the bone replacement material is preferably a bone replacement material for use in the treatment, especially bridging, of bone defects.

It is a particular feature of the bone replacement material that it comprises reinforcing elements and a modelable mass which is curable on contact with water or an aqueous liquid.

In the context of the present invention, the expression "mass which can be modeled" is understood to mean a formable, especially plastically formable, or ductile mass which, in an uncured state, enables accurate filling of a bone defect or part of a bone defect with the bone replacement material or accurate modeling of the bone replacement material onto a bone defect or part of a bone defect.

In the context of the present invention, the expression "reinforcing elements" defines shaped elements which, together with the mass, are crucial for the reinforcing or load-bearing properties of the bone replacement material.

The bone replacement material is especially notable for the following advantages:

The bone replacement material has improved load-bearing capacity over generic bone replacement materials.

The improved load-bearing capacity is based inter alia on the additional use of reinforcing elements which can be held together by the mass even in the uncured state.

An additional improvement in load-bearing capacity is achievable by curing the mass, which consolidates the reinforcing elements within the curing mass.

By applying pressure to the bone replacement material, especially the mass, after levelling or filling of a bone defect and especially prior to curing of the mass, it is possible to additionally increase the integrity of the reinforcing elements.

Furthermore, the mass as such, after curing thereof, contributes to an additional improvement in the load-bearing capacity of the bone replacement material.

The bone replacement material also offers the option of consolidation in stress direction and hence makes an overall contribution to an increase in the durability of the bone replacement material after curing of the mass.

The mass particularly advantageously allows simple portioning of the bone replacement material.

Furthermore, the mass particularly advantageously allows exact levelling or filling of bone defects with the bone replacement material or exact modeling of the bone replacement material to bone defects. This especially also enables treatment of geometrically undefined bone defects.

By varying the proportion of the mass in the bone replacement material, it is possible to regulate the degree of levelling or filling of a bone defect.

It is also advantageous that even bone defects that have arisen or increased in size in the course of revisions can be better filled. It may be sufficient here to treat the bone defects exclusively with the bone replacement material.

Alternatively, the bone replacement material may be intended for bridging of a bone defect, especially of an osseous joint defect.

A further advantage is that the bone replacement material, even after curing of the mass, can be processed mechanically, especially in a material-removing manner, and hence there is no need to remove the bone replacement material in revision operations.

Preferably, the mass is a mass which is modelable under standard conditions, i.e. at 25° C. and 101.325 kPa.

In a preferred embodiment, the mass is a pasty mass. In other words, it is preferable in accordance with the invention when the mass has a pasty consistency or is in the form of a paste.

In a particularly preferred embodiment, the mass is a kneadable mass. In other words, it is particularly preferable in accordance with the invention when the mass has a kneadable consistency or is in the form of a kneadable material or kneading mass. In this embodiment, the bone replacement material can also be referred to as kneadable bone material or a kind of kneadable bone material.

In a particularly preferred embodiment, the reinforcing elements are present in the mass.

In a further embodiment, the reinforcing elements have been wetted or coated with the mass. The reinforcing elements here may have been wetted or coated with the mass only partly, i.e. only over part of the area, or fully, i.e. over the full area.

More particularly, the reinforcing elements may be homogeneously distributed within the mass.

In an embodiment which is advantageous from the point of view of reinforcing and load-bearing capacity, the reinforcing elements are in intermeshing form, especially in mutually interdigitatable, mutually interlockable or mutually interwedgable form.

Preferably, the reinforcing elements are in an intermeshing state. According to the invention, it may especially be the case that the reinforcing elements are in mutually interdigitated, mutually interlocked or mutually interwedged form.

In a further embodiment, the reinforcing elements, preferably by mutual intermeshing, especially mutual interdigitating, interlocking or interwedging, form a three-dimensional framework structure especially having cavities. The cavities of the framework structure are preferably filled with the mass. This form of mutual penetration of mass and reinforcing elements contributes to further improvement in the reinforcing or load-bearing properties of the bone replacement material.

In a further embodiment which is advantageous from the point of view of reinforcing or load-bearing capacity, the reinforcing elements have a porous configuration. A porous configuration of the reinforcing elements has the advantage that the reinforcing elements can be (more easily) compressed, especially deformed, under stress. Corresponding stresses that lead to reinforcing element compression can occur, for example, on application of force to the as yet uncured mass by a medical practitioner implementing treatment or during the curing of the mass. In this way, it is possible to additionally improve mutual consolidation of the reinforcing elements, which in turn results in better load-bearing properties of the bone replacement material.

In a further embodiment, the reinforcing elements and/or the mass include fibers. The fibers may in principle be short and/or long fibers. The fibers are preferably absorbable fibers. More preferably, the fibers are reinforcing fibers, i.e. fibers intended to reinforce the reinforcing elements and/or the mass. In other words, it is preferable when the reinforcing elements and/or the mass have been fiber-reinforced.

In principle, the reinforcing elements may have a porous configuration, i.e. have pores. The pores may be geometrically defined or undefined pores. The pores may have a diameter, especially a mean diameter, of 60 μm to 500 μm, preferably 100 μm to 400 μm.

The reinforcing elements may also especially have a closed-pore or open-pore configuration. An open-pore configuration of the reinforcing elements has the additional advantage that the mass can penetrate into the pores of the reinforcing elements. This allows additional optimization of the reinforcing or load-bearing properties of the bone replacement material.

According to the invention, it may therefore be preferable when a portion of the mass is present in pores of the reinforcing elements.

In a further preferred embodiment, the reinforcing elements have openings or orifices. The openings or orifices may in principle take the form of a depression. However, it is preferable in accordance with the invention when the openings or orifices are in continuous form, i.e. form continuous open inner cavities. In the context of the present invention, the expression "continuously open inner cavities" shall be understood to mean cavities in the reinforcing elements which have at least two openings, especially two opposite openings, to the outside.

The openings or orifices may be circular and/or noncircular, especially polygonal, i.e. in the form of a polygonal line. For example, the openings or orifices may take the form of triangles, quadrangles, pentagons and/or hexagons.

In a more specific embodiment, the openings or orifices have a diameter which permits at least one tension element to pass through. The openings or orifices may have a diameter, for example, of 0.01 mm to 5 mm, especially 0.1 mm to 4 mm, preferably 0.5 mm to 3 mm. By passing the at least one tension element through the openings or orifices of the reinforcing elements, it is possible to secure or to tie the reinforcing elements to one another. The at least one tension element can hold the reinforcing elements together in a comparatively random, i.e. randomized arrangement, or else in a regular arrangement.

According to the invention, it may therefore be the case that the bone replacement material also has at least one tension element, i.e. one tension element or more, especially two or more tension elements. The at least one tension element is preferably guided through continuous openings or orifices of the reinforcing elements, by means of which the reinforcing elements are preferably connected, especially tied, to one another.

The at least one tension element is preferably a textile tension element. For example, the at least one tension element may be a thread (linear thread), especially a monofil or multifil thread. Preferably, the at least one tension element is a surgical suture material.

Alternatively, the at least one tension element may be a textile fabric, especially a loop-formed knit, braid, loop-drawn knit, scrim, nonwoven or nonwoven material. Preferably, the at least one tension element is a mesh, especially a small-pore mesh, preferably a hernia mesh. By incorporating the reinforcing elements into a tension element in mesh form, it is possible to set a regular arrangement of the reinforcing elements. A tension element in mesh form, similarly to a hernia mesh, may have solid node points and/or correspond to a looser scrim which can be displaced into a smaller area.

The at least one tension element may also include or consist of an absorbable and/or non-absorbable material. Suitable materials for the at least one tension element may be selected from the group comprising metals, polymers, inorganic materials and mixtures thereof.

Further advantages which can be implemented when using at least one tension element are described hereinafter.

The use of at least one tension element enables the reinforcing elements to be tied together, which can achieve an immediate increase in strength of the support elements with respect to one another and hence of the bone replacement material. Particularly advantageously, this can lead to a requirement for a smaller amount of the mass envisaged in accordance with the invention in order to obtain a bone replacement material with reinforcement and load-bearing capacity. In addition, it is possible by means of such an increase in strength of the reinforcing elements to lower the risk that a framework structure formed by the reinforcing elements will break up after a brittle fracture. Moreover, by tying the reinforcing elements together, it is particularly advantageously possible to achieve a framework structure with more open pores. It is additionally possible that a tension element-reinforcing element unit (or, if appropriate, multiple tension element-reinforcing element units) can be fixed to an implant and/or a bone and hence secured in a locally stable manner. The tension element-reinforcing element unit (or tension element-reinforcing element units) can be pressed onto the refreshed bone by the securing to the bone and/or the implant. In this way, optimal binding to the bone is possible, and the resulting pressure on the bone promotes bone growth. The transmission of force at the bone defect is preferentially undertaken by the implant. This eliminates the pressure stimulus that induces the bone to form bone (stress shielding). This pressure stimulus can be built up by the tension element-reinforcing element unit(s) that is/are under pressure with respect to the bone.

In a further embodiment, the reinforcing elements are configured such that they can be bonded to one another in a form-fitting, force-fitting and/or cohesive manner. Preferably, the reinforcing elements are configured such that they can be bonded to one another in a form-fitting manner. For example, the reinforcing elements may be configured such that they can be bonded to one another via a plug connector system or in the manner of a plug connector system. The plug connector system may be based here on a peg-hole principle, preferably with an undercut for better anchoring of the reinforcing elements. For this purpose, some of the reinforcing elements may be provided with pegs and other reinforcing elements with appropriate pegholes or slots.

In a further embodiment, the reinforcing elements are bonded to one another in a form-fitting, force-fitting and/or cohesive manner. Preferably, the reinforcing elements are bonded to one another in a form-fitting manner. For example, the reinforcing elements may be bonded to one another via a plug connector system or in the manner of a plug connector system. With regard to the plug connector system, reference is made to the paragraph above.

In a further embodiment, the reinforcing elements are configured such that they can be bonded to an implant in a form-fitting, force-fitting and/or cohesive manner. Preferably, the reinforcing elements are configured such that they can be bonded to an implant in a form-fitting manner. For example, the reinforcing elements may be configured such that they can be bonded to an implant via a plug connector system or in the manner of a plug connector system. The plug connector system may be based on a peg-hole principle. For this purpose, the reinforcing elements may be provided with pegs, and the implant may have complementary pegholes or slots. It is likewise possible in accordance with the invention for these conditions to be reversed.

In a further embodiment, the reinforcing elements are bonded to one another via elongated connecting elements. Preferably, the connecting elements for this purpose project into openings or orifices in the reinforcing elements. With regard to possible configurations of the openings or orifices of the reinforcing elements, reference is made to the preceding remarks. The connecting elements and the reinforcing elements here may comprise or consist of the same material. However, it is preferable when the connecting elements and the reinforcing elements comprise or consist of different materials. Preferably, the reinforcing elements comprise or consist of a more brittle material than the connecting elements. Suitable materials for the connecting elements are absorbable polymers, especially those absorbable over a long period of time, for example polydioxanone, polyhydroxy-alkanoates such as poly(3-hydroxybutyrate) and/or poly-(4-hydroxy butyrate), polyesterurethanes and mixtures thereof.

In a further embodiment, the reinforcing elements have a particle size of 2 mm to 20 mm, preferably 3 mm to 10 mm.

In a further embodiment, the reinforcing elements are in different sizes, especially particle sizes. Through it is possible to achieve mutual interlocking, interdigitation or interwedging of the reinforcing elements.

In principle, the reinforcing elements may have a defined or undefined shape.

It is preferable in accordance with the invention when the reinforcing elements have a defined shape. A defined shape of the reinforcing elements can facilitate mutual anchoring or consolidation of the reinforcing elements.

For example, the reinforcing elements may have a triangular to decagonal outline, especially a quadrangular, pentagonal or hexagonal outline.

In addition, the reinforcing elements, in peripheral direction, may have a spherical outline, especially a ball-shaped or ellipsoidal outline.

In addition, the reinforcing elements may have an (essentially) cylindrical configuration, especially a circular cylindrical configuration.

More particularly, the reinforcing elements may have an (essentially) hollow cylindrical configuration, especially a hollow circular cylindrical configuration.

In addition, the reinforcing elements may have an (essentially) cubic outline.

In addition, the reinforcing elements may have a polyhedral outline, especially a tetra- and/or octahedral outline.

In a particularly preferred embodiment, the reinforcing elements or some of the reinforcing elements are oligopods.

The oligopods may be conical and especially have legs in rotationally symmetric form. The legs here may have a cone angle of 5° to 25°, especially 7° to 15°.

In addition, the oligopods may have legs having a length of 0.5 mm to 5 mm, especially 1.5 mm to 2.5 mm.

In addition, the oligopods may have legs having a mean diameter of 0.2 mm to 3 mm, especially 0.3 mm to 0.7 mm.

The oligopods may also be selected from the group comprising tripods, tetrapods, pentapods, hexapods, heptapods, octapods and mixtures thereof.

It is preferable in accordance with the invention when the reinforcing elements or some of the reinforcing elements are tetrapods. A tetrapodal configuration allows particularly effective mutual intermeshing of the reinforcing elements.

In principle, the bone replacement material may be absorbable, partly absorbable or non-absorbable.

Preferably, the bone replacement material is at least partly absorbable, i.e. partly absorbable or fully absorbable.

If the bone replacement material is partly absorbable, it is preferable when the reinforcing elements are non-absorbable. With regard to the materials that are suitable in this respect, reference is made to the materials elucidated hereinafter.

In the case of a fully absorbable bone replacement material, it may also be advantageous when the materials envisaged for the mass and for the reinforcing elements differ from one another with regard to their absorption characteristics, especially with regard to their duration of absorption.

The reinforcing elements may include an absorbable, partly absorbable or non-absorbable material or consist of such a material.

In order to additionally improve the load-bearing capacity of the bone replacement material, in a further embodiment, the reinforcing elements include a non-absorbable material or consist of such a material. A material of this kind is preferably selected from the group comprising or consisting of metals, alloys, borides, carbides, nitrides, silicides, polymers and mixtures thereof.

Suitable metals may be selected from the group comprising or consisting of titanium, tantalum, niobium, tungsten and zirconium.

Suitable alloys may be selected from the group comprising or consisting of titanium alloys, tantalum alloys, niobium alloys, tungsten alloys and zirconium alloys.

Suitable borides may be selected from the group comprising or consisting of niobium boride, tungsten boride and mixtures thereof.

Suitable carbides may be selected from the group comprising or consisting of aluminum carbide, boron carbide, niobium carbide, silicon carbide, tantalum carbide, titanium carbide, tungsten carbide, vanadium carbide, zirconium carbide and mixtures thereof.

Suitable nitrides may be selected from the group comprising or consisting of boron nitride, chromium nitride, silicon nitride, tantalum nitride, titanium nitride, zirconium nitride and mixtures thereof.

Suitable silicides may be selected from the group comprising or consisting of tantalum silicide, tungsten silicide, zirconium silicide and mixtures thereof.

Suitable (non-absorbable) polymers may be selected from the group comprising or consisting of polymethylmethacrylate (PMMA), polyetheretherketone (PEEK), polyvinyl chloride (PVC), polyethylene (PE), high-density polyethylene (HDPE), ultrahigh molecular weight polyethylene (UHMWPE), polystyrene, polyesters, for example polyethylene terephthalate, polyamides, polypropylene (PP), fluorinated, especially perfluorinated, polymers (such as polytetrafluoroethylene (PTFE), polytrifluorochloroethylene (PTFCE), polyvinyl fluoride (PVF), polyvinylidene difluoride (PVDF), hexafluoropropylene and/or tetrafluoro-ethylene), copolymers thereof and blends thereof.

In a further embodiment, the reinforcing elements include or consist of an absorbable material selected from the group comprising or consisting of calcium compounds such as calcium phosphates, magnesium compounds such as magnesium phosphates, polymers and mixtures thereof.

Suitable (absorbable) polymers may be selected from the group comprising or consisting of polyhydroxyalkanoates, polylactide, polyglycolide, poly-ε-caprolactone, polytrimethylene carbonate, poly-p-dioxanone, proteins, extracellular proteins, collagen, elastin, reticulin, fibronectin, gelatin, polysaccharides, mucopolysaccharides, hyaluronic acid, heparin, heparan sulfate, chondroitin sulfate, dermatan sulfate, keratan sulfate, copolymers thereof and mixtures, especially blends, thereof.

With regard to suitable calcium and/or magnesium compounds, reference is made to the compounds mentioned hereinafter in connection with the mass.

As already mentioned, the mass envisaged in accordance with the invention is curable on contact with water or an aqueous liquid. The aqueous liquid is preferably body fluid, especially bone tissue fluid. Alternatively or additionally, the aqueous liquid may be an aqueous solution, especially aqueous active ingredient-containing solution, for example aqueous salt solution or aqueous medicament-containing solution, or an aqueous suspension.

According to the invention, it may in principle be the case that the curing of the mass is actively initiated prior to introduction, during introduction or after introduction of the bone replacement material into a bone defect by addition of water or an aqueous liquid.

However, it is preferable when, after introduction of the bone replacement material into a bone defect, the mass is cured by contact with bone tissue fluid, especially with interstitial bone tissue fluid. This is advantageous in that a medical practitioner conducting treatment generally has more time available for accurate filling of a bone defect without any risk of premature curing of the mass and hence of the bone replacement material.

In principle, the mass may be curable on contact with water or an aqueous liquid within 15 min to 72 h, preferably 45 min to 18 h.

The mass may also be absorbable, partly absorbable or non-absorbable.

In a particularly preferred embodiment, the mass comprises a solid material which is curable on contact with water or aqueous liquid. The curing of the solid material is preferably based on a cement-like setting reaction with water or an aqueous liquid. More particularly, the solid material may be a bone cement precursor. With regard to the aqueous liquid, reference is made to the preceding remarks.

In a further embodiment, the solid material is a solid mineral material.

The solid material preferably includes a calcium compound, especially a calcium phosphate compound, and/or a magnesium compound, especially a magnesium phosphate compound.

In a further embodiment, the calcium compound is selected from the group comprising or consisting of monocalcium phosphate monohydrate (MCPM), monocalcium phosphate anhydride (MCPA), dicalcium phosphate anhydride (DCPA), dicalcium phosphate dihydrate (DCPD), octacalcium phosphate (OCP), α-tricalcium phosphate (α-TCP), β-tricalcium phosphate (β-TCP), amorphous calcium phosphate (ACP), hydroxylapatite (HA), calcium-deficient hydroxylapatite (CdHA), substituted hydroxylapatite, non-stoichiometric hydroxylapatite, nanoscale hydroxylapatite, tetracalcium phosphate (TTCP), calcium sulfate ($CaSO_4$), calcium sulfate hemihydrate ($CaSO_4 \times 0.5H_2O$), calcium sulfate dihydrate ($CaSO_4 \times 2\ H_2O$), calcium oxide (CaO), calcium hydroxide ($Ca(OH)_2$), calcium carbonate ($CaCO_3$), calcium glycerophosphate, calcium citrate, calcium lactate, calcium acetate, calcium tartrate, calcium chloride ($CaCl_2$), calcium silicate and mixtures thereof.

In a further embodiment, the magnesium compound is selected from the group comprising or consisting of magnesium hydrogenphosphate ($MgHPO_4$) in the form of the hydrates or as an anhydrous substance, trimagnesium phosphate ($Mg_3(PO_4)_2$), magnesium dihydrogenphosphate ($Mg(H_2PO_4)_2$) in the form of the hydrates or as an anhydrous substance, magnesium chloride ($MgCl_2$) in the form of the hydrates or as an anhydrous substance, magnesium glycerophosphate, magnesium hydroxide ($Mg(OH)_2$), magnesium hydroxide carbonate (for example in the form of $4\ MgCO_3 \times Mg(OH)_2 \times 5\ H_2O$), magnesium oxide (MgO), magnesium citrate ($Mg_3(C_6H_5O_7)_2$) or $Mg(C_6H_6O_7)$), calcium magnesium carbonate ($CaMg(CO_3)_2$), dolomite and mixtures thereof.

The solid material is preferably a particulate solid material, especially a powder.

In a further embodiment, the solid material has a proportion of 20% by weight to 90% by weight, preferably 65% by weight to 85% by weight, based on the total weight of the mass.

A particularly high solids content of the mass can be achieved via a broad particle size distribution, especially when >10% of the solid material consists of particles <10 μm and when >10% of the solid material consists of particles >50 μm.

It may also be preferable in accordance with the invention for the reinforcing elements and the mass to include the same absorbable material. The absorbable material is preferably a calcium compound, especially calcium phosphate compound, and/or a magnesium compound, especially magnesium phosphate compound. In this respect, reference is made completely to the preceding remarks.

In a further embodiment, the mass includes an organic carrier liquid, especially in addition to a solid material as described in the preceding embodiments. The carrier liquid is especially intended to impart a modelable consistency to the mass and/or to slow the curing of the mass on contact with water or an aqueous liquid. More particularly, the carrier liquid is intended as a carrier for a solid material as described in the preceding embodiments.

The organic carrier liquid is preferably a non-water-soluble, i.e. water-insoluble, organic carrier liquid.

In an alternative embodiment, the organic carrier liquid is an organic carrier liquid having only low water solubility.

Preferably, the carrier liquid in this embodiment is soluble in water to an extent of <25%, especially <10%, preferably <5%, based on the volume.

The organic carrier liquid may also especially be an oil.

Preferably, the organic carrier liquid is selected from the group comprising or consisting of glycerol triacetate, glycerol tributyrate, glycerol trioleate, glycerol dioleate, glycerol monooleate, capryl caprate, decyl oleate, isopropyl myristate, isopropyl palmitate, oleic acid, oleyl alcohol, oleyl oleate, short-chain triglycerides, mid-chain triglycerides (for example Myritol® 318 PH, Miglyol® 810, Miglyol® 812, Miglyol® 829), short- and mid-chain fatty acid esters of propylene glycol (for example Miglyol® 840), ethyl benzoylacetate, ethyl butyrate, ethyl butyrylacetate, ethyl oleate, ethyl caproate, ethyl caprylate, ethyl caprate, ethyl laurate, ethyl levulinate, ethyl myristate, ethyl palmitate, ethyl linoleate, ethyl stearate, ricinoleic acid, linoleic acid, linolenic acid, arachic acid, oleic acid, ethyl arachidate, α-tocopherol, β-tocopherol, γ-tocopherol, δ-tocopherol, benzyl alcohol, benzyl benzoate, diethyl butylmalonate, diethylene glycol dibutyl ether, diethyl malonate, diethyl phenylmalonate, diethyl phthalate, diethyl sebacate, diethyl subarate, diethyl succinate, dibutyl maleate, dibutyl phthalate, lecithin, paraffin oil, petrolatum, liquid paraffins, esters of sebacic acid, especially dibutyl sebacate, diethyl sebacate, diisopropyl sebacate, dioctyl sebacate and mixtures thereof.

In a further embodiment, the mass further includes a curing regulator, especially a curing accelerator or retardant.

The curing accelerator may especially be a surfactant.

In a more specific embodiment, the surfactant may be selected from the group comprising or consisting of fatty acids and salts thereof, esters of fatty acids and salts thereof, carboxylic ethers, alkyl sulfates, alkyl ether sulfates, alkylsulfonates, sulfosuccinates, monoalkyl phosphates, dialkyl phosphates, acylamino acids and salts thereof, alkylamine salts, alkylimidazolines, tetraalkylammonium salts, tetraarylammonium salts, heterocyclic ammonium salts, ethoxylated amines, amphoteric surfactants, lecithins, fatty alcohols, ethoxylated fatty alcohols, ethylene oxide block copolymers, propylene oxide block copolymers, alkylphenol ethoxylates, alkyl polyglucosides, ethoxylated fats and oils, alkanolamides, ethoxylated alkanolamides, polyethylene glycol fatty acid esters, glycol esters, sorbitan esters (mono- and triesters), sugar esters, ester surfactants, ether surfactants and mixtures thereof.

For example, the surfactant may be selected from the group comprising or consisting of sodium laurylsulfate, glycerol monooleate, polysorbate 20, 21, 40, 60, 61, 65, 80, 81, 85, 120, sorbitan diisostearate, sorbitan dioleate, sorbitan monoisostearate, sorbitan monolaurate, sorbitan monooleate, sorbitan monopalmitate, sorbitan monostearate, sorbitan trioleate, sorbitan trilaurate, sorbitan tricaprylate, sorbitan tricaprate, isopropyl myristate, lecithin, lysolecithins, oleic acid, polyethylene glycol monocetyl ether, polyethylene glycol monostearyl ether, polyethylene glycol monolauryl ether, polyethylene glycol monooleyl ether, polyethoxylated castor oil, polyoxyl-40-stearate, polyoxyl-50-stearate, ascorbyl palmitate, cetyl phosphate and mixtures thereof.

In a further embodiment, the mass also includes a curing accelerator selected from the group consisting of or comprising pyrophosphates, citrates, magnesium ions, calcium carbonate and mixtures thereof.

In a further embodiment, the mass has a proportion of 20% by weight to 80% by weight, preferably 30% by weight to 70% by weight, based on the total weight of the bone replacement material.

In a further embodiment, the reinforcing elements have a proportion of 20% by weight to 80% by weight, preferably 30% by weight to 70% by weight, based on the total weight of the bone replacement material.

In a further embodiment, the bone replacement material, especially the mass and/or the reinforcing elements, includes an active ingredient. The active ingredient may be selected from the group comprising or consisting of physiologically active substances, antibiotics, inflammation-inhibiting medicaments, cytostatics, bone morphogenetic proteins (BMPs), medicaments to combat osteoporosis and mixtures thereof.

For example, the active ingredient may be selected from the group comprising or consisting of BMP 1, BMP 2, BMP 3, BMP 3B, BMP 4, BMP 5, BMP 6, BMP 7, BMP 8A, BMP 8B, BMP 10, BMP 15, interferons, interleukins, especially interleukin-1β, interleukin-6, colony-stimulating factors, chemokines, genamycin, polyhexamethylenebiguanide (PHMB), silver compounds, especially silver salts, preferably in the form of nanoparticles, and mixtures thereof.

In a further embodiment, the bone replacement material is intended for use
  a. in the treatment, especially bridging, of accident-related bone defects,
  b. in the treatment, especially bridging, of inflammatory bone defects,
  c. in the treatment, especially bridging, of tumor-related bone defects,
  d. in the treatment, especially bridging, of osseous joint defects, especially hip joint and/or knee joint defects, preferably of defects of the pelvis, acetabulum, head of femur, neck of femur, femur, fibula and/or tibia,
  e. in the filling of bone defects, preferably in a near-joint region,
  f. in the replacement and/or in the support or lining of stabilizing implants, for example spacer implants, reinforcement rings or wedges, and/or
  g. in the reconstruction of bone tissue.

In other words, the bone replacement material, in a further embodiment, is a bone replacement material intended for use
  a. in the treatment, especially bridging, of accident-related bone defects,
  b. in the treatment, especially bridging, of inflammatory bone defects,
  c. in the treatment, especially bridging, of tumor-related bone defects,
  d. in the treatment, especially bridging, of osseous joint defects, especially hip joint and/or knee joint defects, preferably of defects of the pelvis, acetabulum, head of femur, neck of femur, femur, fibula and/or tibia,
  e. in the filling of bone defects, preferably in a near-joint region,
  f. in the replacement and/or in the support or lining of stabilizing implants, for example spacer implants, reinforcement rings or wedges, and/or
  g. in the reconstruction of bone tissue.

In a second aspect, the invention relates to a process for producing a bone replacement material, especially a bone replacement material according to the first aspect of the invention.

In the process, reinforcing elements and a modelable mass which is curable on contact with water or an aqueous liquid are mixed, and reinforcing elements are especially introduced into a modelable mass which is curable on contact with water or an aqueous liquid.

Alternatively or additionally, (the) reinforcing elements are wetted or coated with a (the) modelable mass which is curable on contact with water or an aqueous liquid.

With regard to further features and advantages of the process, especially of the reinforcing elements and the mass, for avoidance of unnecessary repetition, reference is made completely to the description so far.

In a third aspect, the invention relates to a medical kit.

The kit is preferably intended for use in the treatment, especially bridging, of bone defects. In other words, the kit is preferably a kit for use in the treatment, especially bridging, of bone defects.

More preferably, the kit is intended for use in the production of a bone replacement material, especially a bone replacement material according to a first aspect of the invention, and/or for use in the performance of a process according to the second aspect of the invention. In other words, the kit is more preferably used for production of a bone replacement material, especially a bone replacement material according to the first aspect of the invention, and/or for performing a process according to the second aspect of the invention.

The kit has the following kit components in spatially separate form:
  reinforcing elements and
  a modelable mass which is curable on contact with water or an aqueous liquid.

In a further embodiment, the kit also includes a curing initiator, especially water or an aqueous liquid.

In an embodiment which is advantageous from the treatment point of view, the aqueous liquid includes active ingredients. With regard to suitable active ingredients, reference is made to the description so far.

In a further embodiment, the kit also includes a positioning component for positioning the reinforcing elements and/or the mass, preferably for positioning a bone replacement material obtainable or producible by mixing the reinforcing elements and the mass, in a bone defect. The positioning component may especially be a textile fabric, for example a fabric in the form of a loop-formed knit, a loop-drawn knit, a braid, a scrim, a nonwoven or a nonwoven fabric. Preferably, the positioning component is a mesh, especially a small-pore mesh. More preferably, the positioning component is a medical mesh, especially a hernia mesh.

In a further embodiment, the kit also includes at least one tension element. The at least one tension element is preferably intended to connect reinforcing elements having continuous openings or orifices, i.e. reinforcing elements having an open inner cavity, to one another, and especially to tie them to one another.

The at least one tension element is preferably a textile tension element. For example, the at least one tension element may be a thread (linear thread), especially a monofil or multifil thread. Preferably, the at least one tension element is a surgical suture material.

Alternatively, the at least one tension element may be a textile fabric, especially a loop-formed knit, braid, loop-drawn knit, scrim, nonwoven or nonwoven material. Preferably, the at least one tension element is a mesh, especially a small-pore mesh, preferably a hernia mesh.

The at least one tension element may also include or consist of an absorbable and/or non-absorbable material. Suitable materials for the at least one tension element may be selected from the group comprising metals, polymers, inorganic materials and mixtures thereof.

According to the invention, treatment of a bone defect may especially be accomplished by first positioning reinforcing elements each having a continuous opening or orifice, by means of at least one tension element which is conducted through the openings or orifices of the reinforcing elements, at an implant and/or a bone and then undertaking levelling or filling of the bone defect, especially filling of cavities of a three-dimensional framework structure formed by the reinforcing elements.

In a further embodiment, the kit also includes an implant, especially a bone prosthesis, a joint prosthesis and/or a stabilizing implant, for example a spacer implant, reinforcement ring or wedge.

In a more specific embodiment, the kit is intended for use
a. in the treatment, especially bridging, of accident-related bone defects,
b. in the treatment, especially bridging, of inflammatory bone defects,
c. in the treatment, especially bridging, of tumor-related bone defects,
d. in the treatment, especially bridging, of osseous joint defects, especially hip joint and/or knee joint defects, preferably of defects of the pelvis, acetabulum, head of femur, neck of femur, femur, fibula and/or tibia,
e. in the filling of bone defects, preferably in a near-joint region,
f. in the replacement and/or in the support or lining of stabilizing implants, for example spacer implants, reinforcement rings or wedges, and/or
g. in the reconstruction of bone tissue.

In other words, the kit, in a further embodiment, is a kit for use in at least one of the treatments enumerated above under a. to g.

With regard to further features and advantages of the kit, especially of the reinforcing elements and the mass, to avoid unnecessary repetition, reference is likewise made completely to the description so far.

In a fourth aspect, the invention relates to a further bone replacement material. The bone replacement material includes reinforcing elements having continuous openings or orifices and at least one tension element.

The expression "continuous openings or orifices" means that the openings or orifices form continuous open inner cavities, i.e. cavities in the reinforcing elements which have at least two openings, especially two opposite openings, to the outside.

The at least one tension element is preferably conducted through the openings or orifices of the reinforcing elements, as a result of which the reinforcing elements are connected, especially tied, to one another. Such a manner of connection of the reinforcing elements can achieve particularly advantageous supporting or load-bearing properties of the bone replacement material. In addition, more particularly, the use of a modelable mass curable on contact with water or an aqueous liquid, especially as described in the aspects of the invention so far, may be dispensable.

According to the invention, it may therefore be preferable that the bone replacement material in the fourth aspect of the invention is free of a modelable mass curable on contact with water or an aqueous liquid.

With regard to further features and advantages of the bone replacement material, especially of the reinforcing elements and of the at least one tension element, to avoid unnecessary repetition, reference is likewise made completely to the description so far.

In a fifth aspect, the invention relates to a further medical kit.

The kit is preferably intended for use in the treatment, especially bridging, of bone defects. In other words, the kit is preferably a kit intended for use in the treatment, especially bridging, of bone defects.

More preferably, the kit is intended for use in the production of a bone replacement material according to the fourth aspect of the invention. In other words, the kit is more preferably used for production of a bone replacement material according to the fourth aspect of the invention.

The kit has the following kit components in spatially separate form:
reinforcing elements with continuous openings or orifices and
at least one tension element.

The expression "continuous openings or orifices" means that the openings or orifices form continuous open inner cavities, i.e. cavities in the reinforcing elements having at least two openings, especially two opposite openings, to the outside.

With regard to further features and advantages of the kit, especially of the reinforcing elements and the at least one tension element, to avoid unnecessary repetition, reference is likewise made completely to the description so far.

Further features and advantages will be apparent from the preferred embodiments described hereinafter in the form of examples and from the claims, without restricting the invention thereto. It is possible here for individual features each to be implemented on their own or in combination with one another.

WORKING EXAMPLE

By means of a casting method, tetrapods were cast from a short- and long-fiber-reinforced calcium phosphate cement (CaP cement, PL powder liquid type). For this purpose, two-part silicone molds were produced by means of metal prototypes. The tetrapods were cast in these molds. The tetrapods had an extent of 8 mm. After the calcium phosphate tetrapods had cured, these were encapsulated with a calcium phosphate cement in paste form (CaP cement, Velox, InnoTERE). The samples thus produced had 20% higher flexural strength than the samples that had been produced with a pasty calcium phosphate cement only.

The invention claimed is:

1. A bone replacement material having reinforcing elements and a modelable mass which is curable on contact with water or an aqueous liquid, wherein the reinforcing elements are oligopods and consist of calcium phosphates, magnesium phosphates or mixtures thereof, and wherein the modelable mass includes a solid material which is curable on contact with water or an aqueous liquid and which includes a calcium phosphate compound and/or magnesium phosphate compound, and wherein the curing of the solid material is based on a setting reaction with the water or aqueous liquid, and wherein fiber reinforcing elements are excluded.

2. The bone replacement material of claim 1, characterized in that the mass is a pasty mass.

3. The bone replacement material of claim 1, characterized in that the mass is a kneadable mass.

4. The bone replacement material of claim 1, characterized in that the reinforcing elements are present in the mass.

5. The reinforcing elements of claim 1, characterized in that the reinforcing elements have been wetted or coated with the mass.

6. The bone replacement material of claim 1, characterized in that the reinforcing elements are in intermeshing form.

7. The bone replacement material of claim 1, characterized in that the reinforcing elements form a three-dimensional framework structure having cavities by intermeshing with one another.

8. The bone replacement material as claimed in claim 7, characterized in that the cavities are filled by the mass.

9. The bone replacement material of claim 1, characterized in that some of the mass is present in pores of the reinforcing elements.

10. The bone replacement material of claim 1, characterized in that the reinforcing elements have a particle size of 2 mm to 20 mm or 3 mm to 10 mm.

11. The bone replacement material of claim 1, characterized in that the reinforcing elements are tetrapods.

12. The bone replacement material of claim 1, characterized in that the bone replacement material is at least partly absorbable.

13. The bone replacement material of claim 1, characterized in that the calcium phosphate compound is selected from the group comprising monocalcium phosphate monohydrate (MCPM), monocalcium phosphate anhydride (MCPA), dicalcium phosphate anhydride (DCPA), dicalcium phosphate dihydrate (DCPD), octacalcium phosphate (OCP), α-tricalcium phosphate (α-TCP), β-tricalcium phosphate (β-TCP), amorphous calcium phosphate (ACP), hydroxylapatite (HA), calcium-deficient hydroxylapatite (CdHA), substituted hydroxylapatite, non-stoichiometric hydroxylapatite, nanoscale hydroxylapatite, tetracalcium phosphate (TTCP), and mixtures thereof.

14. The bone replacement material of claim 1, characterized in that the magnesium phosphate compound is selected from the group comprising magnesium hydrogenphosphate (MgHPO4) in the form of the hydrates or as an anhydrous substance, trimagnesium phosphate (Mg3(PO4)2), magnesium dihydrogenphosphate (Mg(H2PO4)2) in the form of the hydrates or as an anhydrous substance, and mixtures thereof.

15. The bone replacement material of claim 1, characterized in that the solid material has a proportion of 20% by weight to 80% by weight or 30% by weight to 70% by weight, based on the total weight of the mass.

16. The bone replacement material of claim 1, characterized in that the reinforcing elements and the mass include the same absorbable material, wherein the absorbable material is a calcium compound and/or magnesium compound.

17. The bone replacement material of claim 1, characterized in that the mass further includes a water-insoluble organic carrier liquid.

18. The bone replacement material of claim 17, characterized in that the carrier liquid is selected from the group comprising glycerol triacetate, glycerol tributyrate, glycerol trioleate, glycerol dioleate, glycerol monooleate, capryl caprate, decyl oleate, isopropyl myristate, isopropyl palmitate, oleic acid, oleyl alcohol, oleyl oleate, short-chain triglycerides, mid-chain triglycerides, short- and mid-chain fatty acid esters of propylene glycol, ethyl benzoylacetate, ethyl butyrate, ethyl butyrylacetate, ethyl oleate, ethyl caproate, ethyl caprylate, ethyl caprate, ethyl laurate, ethyl levulinate, ethyl myristate, ethyl palmitate, ethyl linoleate, ethyl stearate, ricinoleic acid, linoleic acid, linolenic acid, arachic acid, oleic acid, ethyl arachidate, α tocopherol, β tocopherol, γ tocopherol, δ tocopherol, benzyl alcohol, benzyl benzoate, diethyl butylmalonate, diethylene glycol dibutyl ether, diethyl malonate, diethyl phenylmalonate, diethyl phthalate, diethyl sebacate, diethyl subarate, diethyl succinate, dibutyl maleate, dibutyl phthalate, lecithin, paraffin oil, petrolatum, liquid paraffins, esters of sebacic acid, especially dibutyl sebacate, diethyl sebacate, diisopropyl sebacate, dioctyl sebacate and mixtures thereof.

19. The bone replacement material of claim 1, characterized in that the bone replacement material further includes an active ingredient selected from the group comprising physiologically active substances, antibiotics, inflammation-inhibiting medicaments, cytostatics, bone morphogenetic proteins (BMPs), medicaments to combat osteoporosis and mixtures thereof.

20. The bone replacement material of claim 1 for use
  a. in the treatment of accident-related bone defects,
  b. in the treatment of inflammatory bone defects,
  c. in the treatment of tumor-related bone defects,
  d. in the treatment of osseous joint defects,
  e. in the filling of bone defects,
  f. in the replacement of stabilizing implants and/or
  g. in the reconstruction of bone tissue.

21. A process for producing a bone replacement material according to claim 1 in which reinforcing elements and a modelable mass which is curable on contact with water or an aqueous liquid are mixed, and reinforcing elements are introduced into a modelable mass which is curable on contact with water or an aqueous liquid.

22. A medical kit for use in the production of a bone replacement material wherein the kit includes, in spatially separate form:
  a. reinforcing elements; and
  b. a modelable mass which is curable on contact with water or an aqueous liquid, wherein the reinforcing elements are oligopods and consist of calcium phosphates, magnesium phosphates or mixtures thereof, and wherein the modelable mass includes a solid material which is curable on contact with water or an aqueous liquid and which includes a calcium phosphate compound and/or magnesium phosphate compound, and wherein the curing of the solid material is based on a setting reaction with the water or aqueous liquid, and wherein fiber reinforcing elements are excluded.

23. A medical kit for use in the production of a bone replacement material wherein the kit includes, in spatially separate form:
  a. reinforcing elements having continuous openings or orifices, wherein the continuous openings or orifices have a diameter which permits at least one tension element to pass through, and
  b. a modelable mass which is curable on contact with water or an aqueous liquid, wherein the reinforcing elements are oligopods and comprise or consist of calcium phosphates, magnesium phosphates or mixtures thereof, and wherein the modelable mass includes a solid material which is curable on contact with water or an aqueous liquid and which includes a calcium phosphate compound and/or magnesium phosphate compound, and wherein the curing of the solid material is based on a setting reaction with the water or aqueous liquid, and wherein the kit also includes at least one tension element, wherein the at least one tension element is adapted to be guided through the continuous openings or orifices of the reinforcing elements to connect the reinforcing elements to one another.

* * * * *